United States Patent

Jones

[11] 4,137,117
[45] Jan. 30, 1979

[54] METHOD OF MAKING A SOLVENT-BONDED JOINT

[75] Inventor: Eugene C. Jones, Laguna Niguel, Calif.

[73] Assignee: American Hospital Supply Corporation, Evanston, Ill.

[21] Appl. No.: 776,430

[22] Filed: Mar. 10, 1977

[51] Int. Cl.² .............................................. B29C 27/02
[52] U.S. Cl. .................................. 156/294; 156/305; 156/306; 285/21; 285/22; 285/260; 285/423; 285/DIG. 16; 285/20
[58] Field of Search ............... 156/294, 305, 307, 308, 156/293, 306; 285/21, 22, 260, 423, DIG. 16, 20

[56] References Cited

U.S. PATENT DOCUMENTS

| | | | |
|---|---|---|---|
| 2,302,244 | 11/1942 | Morrell | 285/22 |
| 2,686,091 | 8/1954 | Young | 156/294 |
| 2,983,639 | 5/1961 | Jageman | 156/294 |
| 3,473,833 | 10/1969 | Bremer | 285/423 |
| 3,539,205 | 11/1970 | Johnson et al. | 285/423 |
| 3,700,531 | 10/1972 | Schruff et al. | 156/305 |
| 3,765,983 | 10/1973 | Putzier | 156/294 |
| 3,768,476 | 10/1973 | Raitto | 285/423 |
| 3,830,173 | 8/1974 | Hubble et al. | 156/294 |
| 3,920,787 | 11/1975 | McDowell et al. | 285/21 |
| 4,004,586 | 1/1977 | Christensen et al. | 285/260 |

*Primary Examiner*—William A. Powell
*Assistant Examiner*—Jerome W. Massie
*Attorney, Agent, or Firm*—Tilton, Fallon, Lungmus & Chestnut

[57] ABSTRACT

A solvent-bonded joint between plastic members, and a method of making the same, particularly useful where such members are intended to convey flowable materials such as sterile medical solutions. The joint includes a pair of members joined at a zone of interference, a tapered crevice between the members, a solvent bond in the tapered crevice, and a series of spacers extending along the entrance to the crevice. The spacers or nubs are provided by one or both of the members and maintain the walls at the entrance of the crevice in uniformly-spaced and stressed condition to facilitate introduction of solvent and to insure proper bonding of the parts even where such parts are formed of flexible plastic material. The zone of interference serves as a barrier against any flowable material entering the tapered crevice in the opposite direction prior to formation of the solvent bond and further serves as a barrier against the escape of solvent through the crevice or the contamination by solvent of any material beyond or below the crevice.

16 Claims, 7 Drawing Figures

U.S. Patent Jan. 30, 1979 4,137,117
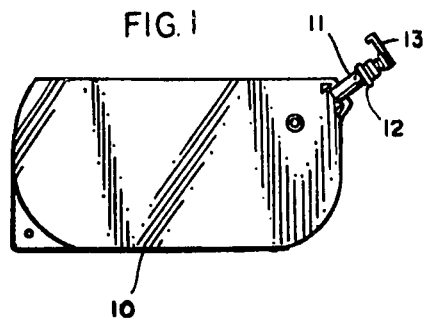
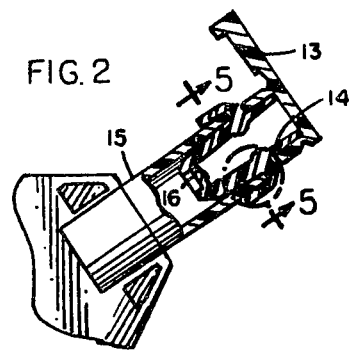
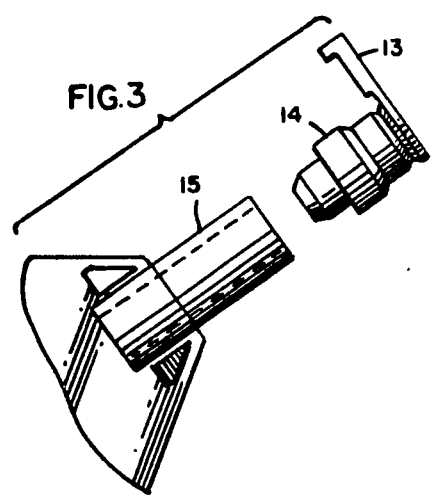
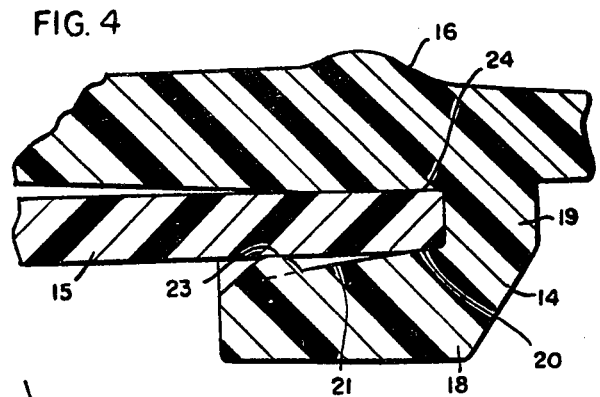
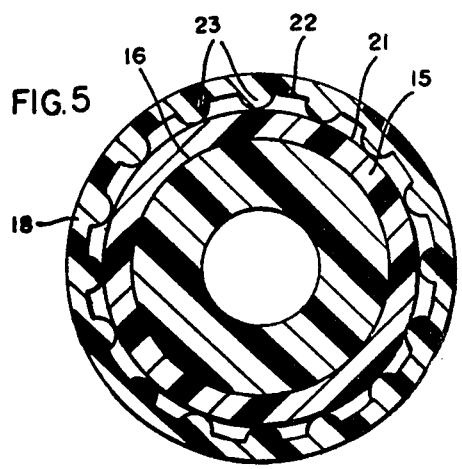
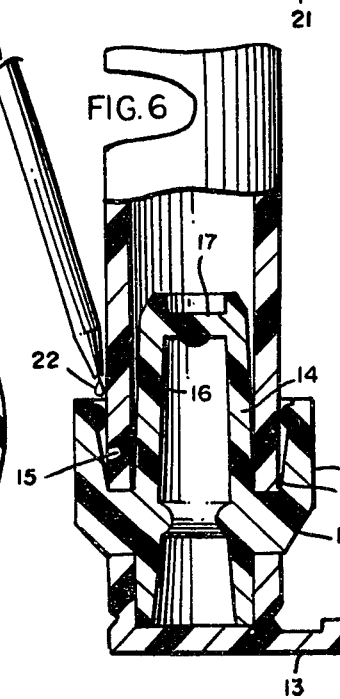
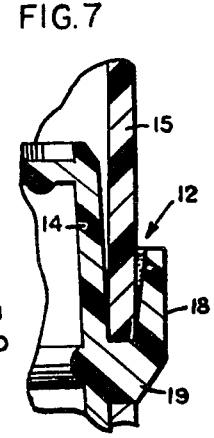

METHOD OF MAKING A SOLVENT-BONDED JOINT

BACKGROUND

Various methods have been used in the past for permanently joining plastic parts in fluid-tight sealing relation, including heat sealing and solvent-bonding techniques. Heat sealing, although widely used, ordinarily requires elaborate supports and operating mechanisms to achieve reliability and production volume in the assembly of relatively small plastic parts such as, for example, filter housing, couplings, port assemblies, and other elements and assemblies commonly used in medical equipment.

Solvent sealing, which ordinarily involves coating one of the parts with solvent before the two parts are fitted together, is suitable for some operations but has severe limitations for volume production. Parts once coated must be immediately assembled; it is not feasible, for example, to coat successively a multiplicity of parts and then assemble them in a batch-type operation. Also, in those cases where one of the parts contains (or communicates with) a liquid, the usual solvent coating and fitting operations are not only awkward and unwieldly, but present risks of liquid interfering with proper solvent bonding and, even more important, of small amounts of solvent invading the liquid-containing compartment. It is apparent that any contact between the liquid or solvent is undesirable and, especially if it might result in contamination of the liquid (such as parenteral fluid), must be strictly avoided.

SUMMARY

The solvent joint of this invention involves a pair of plastic parts or members frictionally engageable in a liquid-tight zone of interference, a tapered crevice between those members leading to the zone of interference with the zone of interference serving as a barrier against flow in either direction through the apex of the tapered crevice, and a permanent solvent bond between the members in at least the base of the tapered crevice. One or both of the plastic members is formed of resilient or flexible plastic material and, in the embodiment disclosed, the members are tubular with one of the members receiving the other in telescoping or overlapping relationship. The receiving member has an outer skirt which, together with the main portion of the receiving member, defines an annular channel or recess for receiving the end portion of the other telescoping member.

A series of uniformly- and circumferentially-spaced nubs or projections, formed integrally with at least one of the members, extends about the mouth of the crevice at the time of solvent introduction and serves to maintain the parts in concentric relation, with the mouth of the crevice at uniform width, throughout solvent sealing, thereby insuring the formation of a circumferentially-uniform solvent bond between the parts. The nubs may also contribute in retaining solvent immediately following its introduction and in providing a visual indication when the preferred amount of solvent has been introduced. When solvent has been added to the optimum level or extent, evaporation of such solvent is accompanied by concurrent dissolving of the nubs so that upon completion of the solvent bonding step the nubs are substantially if not entirely dissolved and the plastic thereof is reformed as part of the joint.

It is therefore an object of this invention to provide a solvent-bonded joint, and its method of formation, between a pair of flexible plastic tubular members so that the resulting joint or union will be suitable for carrying flowable materials, especially liquids such as sterile medical liquids suitable for use in surgery or for administration to patients. The provision of the structure and the realization of the advantages derived therefrom constitute additional important objects of this invention. Other objects of the invention can be appreciated from the details of construction and operation set forth in the accompanying specification, claims, and drawings.

DRAWINGS

FIG. 1 is a front elevational view of a bag adapted for use in the administration of medical liquid, the bag utilizing the solvent-bonded joint and method of this invention.

FIG. 2 is a longitudinal sectional view showing the assembled parts just prior to solvent introduction and fusion.

FIG. 3 is a side elevational view showing the parts in exploded condition.

FIG. 4 is a greatly enlarged longitudinal sectional view of a portion indicated by a circle in FIG. 2.

FIG. 5 is an enlarged transverse cross sectional view taken along line 5-5 of FIG. 2.

FIG. 6 is an enlarged longitudinal sectional view showing the joint of the present invention during introduction of a solvent to form the solvent bond.

FIG. 7 is a fragmentary sectional view similar to FIG. 6 but showing the parts following solvent fusion.

DESCRIPTION

In the illustration given, and with reference first to FIG. 1, the numeral 10 generally designates a parenteral fluid administration bag having an outlet port assembly 11. The port assembly includes a solvent joing 12 (FIG. 7) formed in accordance with this invention. The solvent joint is particularly well suited for use in such medical liquid administration equipment for operatively connecting the components together even where one of the components (such as the bag of this illustration) contains such liquid at the time the solvent joint is formed.

The outlet portion assembly 11 includes a tear cap 13, a port closure 14, and an outlet tube or neck 15. The tube has one end attached to a corner of the bag 10 and communicates with the interior of that bag. Port closure 14 includes a tubular insert portion 16 which is received within the end of neck or tube 15 and which terminates in a diaphragm 17. The port closure also has a concentric outer skirt portion 18 which extends about the insert portion and is joined thereto by integral connecting portion 19.

The solvent joint 12 is formed between a pair of plastic members or parts which, in the illustration given, constitute the outlet tube or neck 15 and the outer portion or skirt 18 of port closure 14. It is to be understood, however, that the joint is shown as being operatively associated with an outlet port assembly primarily for purposes of illustrating one of the many advantageous applications of this invention. Accordingly, the solvent joint in the following description is equally well suited for joining plastic members of many different configurations within the contemplation of the present invention.

Referring to FIGS. 4 and 5, in which the parts are shown just prior to solvent introduction and fusion, members 15 and 18 are in fluid-tight frictional contact along an annular zone of interference 20. That zone of interference takes the form of direct sealing contact between the inner surface of skirt member 18 near the base thereof and the outer surface of tube member 15 adjacent its free end. A tapered crevice 21 extends from the free end of skirt member 18 to the zone of interference 20.

In the embodiment shown, member 18 is provided with a plurality of uniformly- and circumferentially-spaced enlargements or nubs 23 which bear against the outer surface of member 15 and which extend in a series substantially parallel with, but spaced from, the zone of interference 20. FIG. 4 reveals that the nubs or projections are disposed near the free end of skirt portion 18, that is, adjacent the mouth or entrance to the crevice and at a substantial axial distance from interference zone 20.

A second zone of interference 24 is located between the inner surface of port tube 15 (adjacent the end of that tube) and the outer surface of the base of insert 16. Therefore, insertion of the port 15 into the annular recess of the port closure 14 results in the formation of two fluid-tight sealing zones 20 and 24 with the enlargements or projections 23 of member 18 bearing forceably against the outer surface of member 15. The projections control the configuration of the tapered crevice 21, maintaining its dimensions substantially uniform throughout the entire circumference of the assembly and insuring that solvent introduced after the parts have been so pre-assembled will be distributed uniformly by a capillary action regardless of the circumferential location of solvent introduction.

It is believed apparent that the invention is of particular importance where the cooperating members 15 and 18, or at least the latter of these members, are formed of flexible plastic material. Any flexible plastic material capable of being solvent bonded may be used. Examples are plasticized polyvinyl chloride and styrene butadiene; however, other solvent-bondable plastic materials having similar properties are well known and may be used.

The circumscribing skirt portion 18, which may be regarded as an overlapping or receiving member, has an inner surface which forms an angle of about 1 to 20 degrees, and preferably 2 to 6 degrees, with respect to the outer surface of member 15. Stated differently, in the preferred form of the invention the taper of crevice 21 is approximately 2 to 6 degrees. Such a relationship insures that solvent will wick into the crevice to the zone of interference 20 and will remain in the crevice even if the parts are inverted immediately following introduction of the solvent.

The method of joining the parts is as follows: The parts are first fitted together in frictional engagement as shown in FIGS. 2, 4, and 5. Precise relative positioning of the parts is easily achieved because no solvent is yet present and fusion has therefore not commenced. When the parts are properly interfitted, zone of interference 24 is formed and serves primarily as a liquid-tight barrier to block the flow of liquid (or other flowable material) from bag 10 to the tapered crevice 21 where it might otherwise wet the surfaces of that crevice and prevent the formation of an effective solvent bond.

The solvent bond 12 is formed by introducing solvent 22 into the mouth of the crevice as indicated in FIG. 6. The liquid solvent spreads uniformly about member 15 within the crevice, exposing the opposing surfaces of the parts to uniform solvent action. While the amount of solvent might be varied according to preference, in the best mode presently known for practicing the invention a sufficient volume of solvent is added to surround the nubs or projections 23. Under such circumstances, the nubs serve as a gauge to indicate whether a sufficient solvent volume has been introduced. If the solvent bridges the space between adjacent nubs, then the volume of added solvent is at or near its optimum level.

Following addition of liquid solvent 22, the solvent begins to evaporate and also commences to dissolve the strata of plastic material in direct contact therewith. The final solvent-formed bond 12 results when evaporation is completed. At that time the parts assume the relationship somewhat schematically depicted in FIG. 7. It is to be understood that the material illustrated in the crevice and designated by a stippled shading, is resolidified plastic from members 14 and 15. Hence, the joint is a fusion joint and in actual practice the material in the previously-existing crevice is visually indistinguishable from the plastic members themselves. Furthermore, where the joint is formed by adding solvent to a level at or above projections 23, such projections no longer exist in their original form, at least to any appreciable extent, in the final joint. After functioning as spacers to insure uniform distribution of solvent within the crevice, such projections themselves dissolve, at least partly because of their relatively great surface area, and become part of the resolidified mass of material which fuses the parts together.

As the solvent is evaporating, intereference zone 20 performs the function of blocking the escape of solvent through the apex of the crevice. Therefore, the two zones of interference, zones 20 and 24, together prevent contact between the liquid (or other flowable material) within the bag and the solvent introduced to form the permanent joint, eliminating the risk of contaminating the contents of the bag by solvent, and also reduce the danger that the flowable contents of the bag might impair the formation of an effective solvent bond. The result, following introduction of the solvent and evaporation thereafter, is a permanent solvent bond 12 which provides a contamination-proof and leak-proof joint between the parts.

The solvent 22 may be formulated from any of a variety of well-known plastic solvents such as, for example, cyclohexanone or tetrahydrofuran. As used herein, the term "solvent" means any liquid bonding agent which has some capability of dissolving or softening the plastic material or materials from which the parts are formed, even though such agent may also contain fillers or other ingredients which have no such properties. Thus, a bodied solvent, or a cement having a liquid medium which is also a solvent for the plastic materials, is regarded as a solvent within the meaning of this application.

While in the foregoing specification a detailed description of the invention has been set forth for the purpose of illustration, variation of the details herein given may be made by those skilled in the art without departing from the spirit and scope of the invention.

I claim:

1. A method of joining two plastic members, comprising the steps of fitting said members together in frictional engagement to form a fluid-tight zone of interference between opposing side surfaces of said members and with a tapered crevice between said surfaces leading to said zone, simultaneously spacing said members apart by means of spaced points of contact disposed in a series along the entrance to said crevice and spaced longitudinally from said zone of interference, and thereafter introducing a solvent into said tapered crevice and between said points of contact to form a solvent bond between said members.

2. The method of claim 1 in which said series extends along a line parallel to said zone of interference.

3. The method of claim 2 in which said members are tubular, one of said members telescopingly receiving an end portion of the other of said members in overlapping relationship.

4. The method of claim 3 in which the overlapping portions of said members define said tapered crevice and said end of said telescoping member frictionally engages said end of the receiving member at said zone of interference.

5. The method of claim 4 in which said crevice tapers at an angle of about 1 to 20 degrees.

6. The method of claim 5 in which said angle is within the range of about 2 to 6 degrees.

7. The method of claim 4 in which said receiving member includes a tubular insert portion disposed within said other of said members, said insert portion engaging said other of said members to form a second zone of interference.

8. The method of claim 1 in which said plastic members are formed of flexible plastic material.

9. A method of joining two plastic members, comprising the steps of fitting said members together in frictional engagement to form a fluidtight zone of interference between opposing side surfaces of said members and with a tapered crevice between said surfaces leading to said zone, simultaneously spacing said members apart by means of spaced points of contact disposed in a series along the entrance to said crevice and spaced longitudinally from said zone of interference, and thereafter introducing a solvent into said tapered crevice and between said points of contact to form a solvent bond between said members, said spaced points of contact being defined by integral projections from at least one of said members, said step of introducing solvent including the introduction of sufficient solvent into said crevice to surround said projections with solvent and cause substantial dissolving of the same.

10. A method for joining two tubular plastic members, comprising the steps of telescopingly fitting the end portion of an outer member over the end portion of an inner member to define a fluidtight zone of interference between opposing side surfaces of such members and to form an annular crevice having an open mouth and extending from the free end of the outer member to said zone of interference, simultaneously spacing said free end of said outer member from said inner member along a circumferential series of uniformly-spaced points of contact therebetween, said points of contact being spaced longitudinally from said zone of interference, and thereafter introducing a solvent into the open mouth of said tapered crevice to form a solvent bond between said inner and outer members.

11. The method of claim 10 in which said series extends along a line parallel to said zone of interference and adjacent to the mouth of said crevice.

12. The method of claim 10 in which said crevice tapers at an angle of about 1 to 20 degrees.

13. The method of claim 12 in which said angle falls within the range of about 2 to 6 degrees.

14. The method of claim 10 in which said outer member includes a tubular insert portion disposed within said inner member, said insert portion engaging the inner surface of said inner member to form a second zone of interference.

15. The method of claim 10 in which said tubular members are formed of flexible plastic material.

16. A method for joining two tubular plastic members, comprising the steps of telescopingly fitting the end portion of an outer member over the end portion of an inner member to define a fluidtight zone of intereference between opposing side surfaces of such members and to form an annular crevice having an open mouth and extending from the free end of the outer member to said zone of interference, simultaneously spacing said free end of said outer member from said inner member along a circumferential series of uniformly-spaced points of contact therebetween, said points of contact being spaced longitudinally from said zone of interference, and thereafter introducing a solvent into the open mouth of said tapered crevice to form a solvent bond between said inner and outer members, said spaced points of contact being defined by integral projections from one of said members engaging the other of said members adjacent the mouth of said crevice, said solvent being introduced in a quantity sufficient to substantially dissolve said projections in the form of said solvent bond.

* * * * *